US009566156B2

(12) United States Patent
Monaghan et al.

(10) Patent No.: US 9,566,156 B2
(45) Date of Patent: *Feb. 14, 2017

(54) COMPOSITE DEVICE THAT COMBINES POROUS METAL AND BONE STIMULI

(71) Applicant: Zimmer, Inc., Warsaw, IN (US)

(72) Inventors: Matthew E. Monaghan, Fort Wayne, IN (US); Timothy A. Hoeman, Morris Plains, NJ (US)

(73) Assignee: Zimmer, Inc., Warsaw, IN (US)

( * ) Notice: Subject to any disclaimer, the term of this patent is extended or adjusted under 35 U.S.C. 154(b) by 132 days.

This patent is subject to a terminal disclaimer.

(21) Appl. No.: 14/283,598

(22) Filed: May 21, 2014

(65) Prior Publication Data

US 2014/0257513 A1    Sep. 11, 2014

Related U.S. Application Data

(63) Continuation of application No. 13/736,577, filed on Jan. 8, 2013, now Pat. No. 8,790,402.

(Continued)

(51) Int. Cl.
*A61F 2/28* (2006.01)
*A61L 27/04* (2006.01)
(Continued)

(52) U.S. Cl.
CPC ................. *A61F 2/28* (2013.01); *A61L 27/04* (2013.01); *A61L 27/54* (2013.01); *A61L 27/56* (2013.01); *A61L 27/58* (2013.01); *A61F 2002/2835* (2013.01); *A61L 2300/412* (2013.01); *A61L 2430/02* (2013.01)

(58) Field of Classification Search
CPC .......... A61F 2/28; A61F 2/389; A61F 2/3868; A61F 2/367
See application file for complete search history.

(56) References Cited

U.S. PATENT DOCUMENTS 5,124,952 A    6/1992  Knize et al.
5,282,861 A    2/1994  Kaplan
(Continued)

FOREIGN PATENT DOCUMENTS

CN         1033673 A      7/1989
CN       101082276 A     12/2007
(Continued)

OTHER PUBLICATIONS

"U.S. Appl. No. 13/736,577, Non Final Office Action mailed Jan. 29, 2014", 6 pgs.

(Continued)

*Primary Examiner* — Jason-Dennis Stewart
(74) *Attorney, Agent, or Firm* — Schwegman Lundberg & Woessner, P.A.

(57) ABSTRACT

An orthopedic implant for filling voids in bones, and methods of using the same. The orthopedic implant comprises an open porous metal component, having pores for promoting bone regeneration, and a resorbable bone growth promoting component which is resorbed into new bone. The orthopedic implant and methods of the present disclosure provide structural support for the bone as well as osteoconductive and/or osteoinductive matrix for promoting bone re-growth within bone void. Advantageously, the orthopedic implants and methods disclosed herein are useful in filling critically sized bone voids.

19 Claims, 9 Drawing Sheets

Related U.S. Application Data (60) Provisional application No. 61/584,460, filed on Jan. 9, 2012.

(51) Int. Cl.
*A61L 27/54* (2006.01)
*A61L 27/56* (2006.01)
*A61L 27/58* (2006.01)

(56) References Cited

U.S. PATENT DOCUMENTS

| | | | |
|---|---|---|---|
| 5,290,763 | A | 3/1994 | Poser et al. |
| 5,926,437 | A | 7/1999 | Ortiz |
| 6,151,554 | A | 11/2000 | Rodney |
| 6,462,549 | B1 | 10/2002 | Curtis et al. |
| 7,718,616 | B2 | 5/2010 | Thorne |
| 8,790,402 | B2 | 7/2014 | Monaghan et al. |
| 2005/0272153 | A1 | 12/2005 | Xuenong et al. |
| 2009/0112315 | A1 | 4/2009 | Fang et al. |
| 2011/0165199 | A1 | 7/2011 | Thorne et al. |
| 2013/0178946 | A1 | 7/2013 | Monaghan et al. |

FOREIGN PATENT DOCUMENTS

| | | |
|---|---|---|
| CN | 101766839 A | 7/2010 |
| CN | 104159621 A | 11/2014 |
| WO | WO-2013106318 A1 | 7/2013 |

OTHER PUBLICATIONS

"U.S. Appl. No. 13/736,577, Notice of Allowance mailed May 6, 2014", 8 pgs.

"U.S. Appl. No. 13/736,577, Response filed Apr. 28, 2014 to Non Final Office Action mailed Jan. 29, 2014", 7 pgs.

"U.S. Appl. No. 13/736,577, Response filed Dec. 9, 2013 to Restriction Requirement mailed Nov. 8, 2013", 7 pgs.

"U.S. Appl. No. 13/736,577, Restriction Requirement mailed Nov. 8, 2013", 8 pgs.

"International Application Serial No. PCT/US2013/020656, International Search Report mailed May 16, 2013", 5 pgs.

"International Application Serial No. PCT/US2013/020656, Written Opinion mailed May 16, 2013", 6 pgs.

Levine, Brett R, et al., "Experimental and clinical performance of porous tantalum in orthopedic surgery", Biomaterials, (27), (Sep. 2006), 4671-81.

Li, Jiaping, et al., "Biological performance in goats of a porous titanium alloy-biphasic calcium phosphate composite", Biomaterials, Elsevier Science Publishers vol. 28, No. 29, (Aug. 10, 2007), 4209-4218.

"Australian Application Serial No. 2013208168, Patent Examination Report No. 1 Mailed Nov. 5, 2015", 5 pgs.

"Australian Application Serial No. 2013208168, Response Filed Feb. 18, 2016 Patent Examination Report No. 1 Mailed Nov. 5, 2015", 24 pgs.

"Australian Application Serial No. 2013208168, Response filed May 3, 2016 to Subsequent Examiners Report mailed Mar. 16, 2016", 19 pgs.

"Australian Application Serial No. 2013208168, Subsequent Examiners Report mailed Mar. 16, 2016", 3 pgs.

"Chinese Application Serial No. 201080066459.1, Office Action mailed Feb. 28, 2015", (w/ English Translation), 31 pgs.

"Chinese Application Serial No. 201380013104.X, Office Action mailed Mar. 30, 2015", 6 pgs.

"Chinese Application Serial No. 201380013104.X, Office Action mailed Apr. 25, 2016", 8 pgs.

"Chinese Application Serial No. 201380013104.X, Office Action mailed Nov. 10, 2015", 13 pgs.

"Chinese Application Serial No. 201380013104.X, Response filed Jan. 25, 2016 to Office Action mailed Nov. 10, 2015", 5 pgs.

"Chinese Application Serial No. 201380013104.X, Response filed Aug. 12, 2015 to Office Action mailed Mar. 30, 2015", 8 pgs.

"Chinese Application Serial No. 201380013104.X, Voluntary Amendment filed Feb. 12, 2015", 6 pgs.

"International Application Serial No. PCT/US2013/020656, International Preliminary Report on Patentability mailed Jul. 24, 2014", 7 pgs.

COMPOSITE DEVICE THAT COMBINES POROUS METAL AND BONE STIMULI

CLAIM OF PRIORITY

This application is a continuation of U.S. patent application Ser. No. 13/736,577, filed on Jan. 8, 2013, which claims the benefit of priority under 35 U.S.C. §119(e) of Monaghan et al., U.S. Provisional Patent Application Ser. No. 61/584,460, entitled "COMPOSITE DEVICE THAT COMBINES POROUS METAL AND BONE STIMULI", filed on Jan. 9, 2012, each of which is herein incorporated by reference in its entirety.

BACKGROUND

1. Field of the Disclosure

The present disclosure relates to orthopaedic implants for filling voids in bones. More particularly, the present disclosure relates to orthopaedic implants having a porous metal component and a resorbable bone growth promoting component for filling voids in bones, and methods of using the same.

2. Description of the Related Art

Bone voids may result for a number of reasons. For example, joint injuries or disease may result in the formation of defects and voids in a bone. Additionally, many surgical procedures require drilling into bone, thereby creating bone voids. Further, the locations at which bone voids occur, and the size of bone voids, are patient specific.

In some cases, a bone void may be so large that the natural bone is unable to fill the void naturally. Such a void is referred to as a "critical size" bone void, and may lead to functional impairment of the bone. The critical size for a bone void is dependent on the patient and the location at which the bone void occurs. Thus, the use of standard implants for filling bone voids, especially critical size bone voids, may not be possible.

SUMMARY

The present disclosure relates to orthopaedic implants and methods of utilizing the same for filling voids in bones. The orthopaedic implants and methods of the present disclosure provide structural support for the bone, as well as an osteoconductive and/or osteoinductive matrix for promoting bone re-growth within bone voids. Advantageously, the orthopaedic implants and methods disclosed herein are useful in filling uniquely-shaped and critically-sized bone voids.

According to an embodiment of the present disclosure, an orthopaedic implant for treating a bone void is provided. The orthopaedic implant includes an open porous metal component and a resorbable bone growth promoting component. The porous metal component includes a first porous metal layer spaced apart from a second porous metal layer. This spacing can include a first layer of the resorbable bone growth promoting component situated between the two porous metal layers. For example, the first layer of the resorbable bone growth component can contact both the first and second porous metal layers although this sort of arrangement of layers is not necessary to broader aspects of the disclosure. In some embodiments, the first and the second porous metal layers of the porous metal component comprise a coefficient of friction which is greater than the resorbable bone growth promoting component and greater than mammalian bone tissue. Additionally, the orthopaedic implant can include an implantable prosthesis with an elongate stem component that traverses the first porous metal layer and the second porous metal layer such that the first porous metal layer and the second porous metal layer are generally transverse to a longitudinal axis of the elongate stem component. In some aspects, the elongate stem component will include an open porous metal outer surface that can contact portions of the porous metal layers.

In another embodiment, the present disclosure provides an orthopaedic implant that incorporates an implantable prosthesis and a three-dimensional augment body. The augment body provides an elongate passage into which an elongate stem component of the implantable prosthesis can be received for augmenting the implantable prosthesis. Additionally, the augment body incorporates a plurality of stacked layers which includes a first open porous metal layer, a second open porous metal layer, and a resorbable bone growth-promoting layer that is situated between the first open porous metal layer and the second open porous metal layer. In some aspects, a top face of the resorbable bone growth-promoting layer contacts a bottom face of the first open porous metal layer, and a bottom face of the resorbable bone growth-promoting layer contacts a top face of the second open porous metal layer.

In another embodiment, the present disclosure provides a method of implanting an orthopaedic implant. In this particular method, a three-dimensional augment body is positioned in a bone with an elongate stem component of an implantable prosthesis received in an elongate passage in the augment body. The augment body incorporates a plurality of stacked layers which includes a first open porous metal layer spaced from a second open porous metal layer. The elongate stem component, which in some aspects can include an open porous metal outer surface, traverses the first open porous metal layer and the second open porous metal layer. In some forms, one or more resorbable bone growth-promoting layers are situated between the first open porous metal layer and the second open porous metal layer. Additionally, the augment body can be positioned in the bone before, after, or concurrently as the elongate stem component of the implantable prosthesis is received in the elongate passage.

In another embodiment, the present disclosure provides a method of implanting an orthopaedic implant. In one step, a multilayered malleable sheet is positioned in a bone void with a first face of the malleable sheet contacting walls of the bone void and a second face of the malleable sheet remaining exposed for contacting an implantable prosthesis that is subsequently implantable adjacent the bone void. The multilayered malleable sheet incorporates a first open porous metal layer spaced from a second open porous metal layer. In another step, an implantable prosthesis is located adjacent the bone void so as to contact the exposed second face of the malleable sheet. One or more resorbable bone growth-promoting layers can be situated between and/or to either side of each of the first open porous metal layer and the second open porous metal layer.

According to another embodiment of the present disclosure, an orthopaedic implant is provided. The orthopaedic implant includes a monolithic open porous metal body having a plurality of channels therein and an exposed porous exterior surface for contacting bone. The orthopaedic implant also includes a resorbable bone growth promoting component which comprises an osteoconductive carrier, and at least one bone growth factor. Further, the resorbable bone growth promoting component is disposed within the channels of the monolithic open porous metal body of the orthopaedic implant. In some embodiments, the resorbable bone growth promoting component substantially fills the channels of the monolithic open porous metal body.

BRIEF DESCRIPTION OF THE DRAWINGS

The above-mentioned and other features and advantages of this disclosure, and the manner of attaining them, will become more apparent and the disclosure itself will be better understood by reference to the following description of embodiments of the disclosure taken in conjunction with the accompanying drawings, wherein:

FIG. 5b is an enlarged view of the orthopaedic implant implanted within the bone void of FIG. 5a;

FIG. 6a is a cross-sectional view illustrating an orthopaedic implant according to the present disclosure implanted within a void in an acetabulum;

FIG. 6b is an enlarged view of the orthopaedic implant implanted within the void of FIG. 6a;

FIG. 9b is an enlarged perspective view of another embodiment of the orthopaedic implant of FIG. 9a.

Corresponding reference characters indicate corresponding parts throughout the several views. The exemplifications set out herein illustrate exemplary embodiments of the disclosure and such exemplifications are not to be construed as limiting the scope of the disclosure in any manner.

DETAILED DESCRIPTION

Introduction.

The present disclosure generally relates to orthopaedic implants for filling voids in bones and methods of utilizing the orthopaedic implants disclosed herein. The orthopaedic implants disclosed herein comprise an open porous metal component and a resorbable bone growth promoting component. Further, the orthopaedic implants disclosed herein provide structural support for the bone as well as an osteoconductive and/or osteoinductive matrix for promoting bone re-growth within the bone void. Advantageously, the orthopaedic implants disclosed herein may be used to fill critically sized bone voids.

Open Porous Metal Component.

1. Structure of Open Porous Metal Component.

Figure 1:
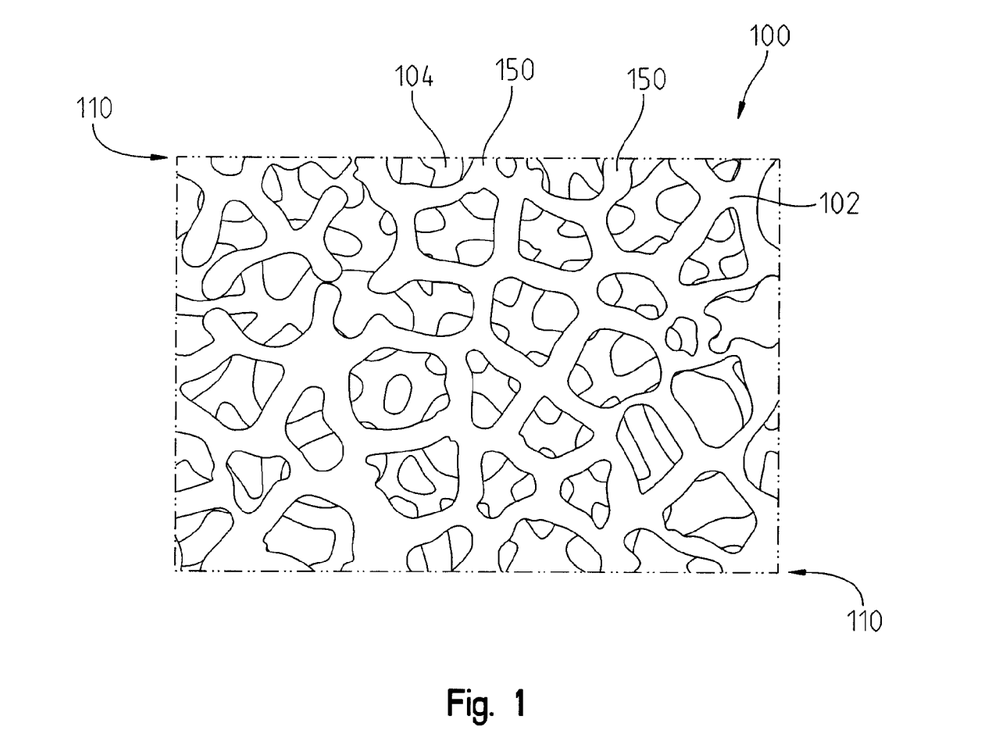
FIG. 1 is an enlarged cross-sectional view of the structure of an open porous metal component according to the instant disclosure.

The orthopaedic implants disclosed herein are comprised, in part, of open porous metal component 100 (FIG. 1). According to some embodiments of the orthopaedic implants disclosed herein, open porous metal component 100 may comprise all, or a substantial portion of, the implant. As described herein, open porous metal component 100 provides structural support to the orthopaedic implants and to the bone, within a bone void. Additionally, open porous metal component 100 comprises one or more exposed porous metal surfaces 110 which, as described herein, are particularly suited for contacting bone and for promoting bone ingrowth therein.

Referring to FIG. 1, an illustrative embodiment of open porous metal component 100 is depicted. As shown, open porous metal component 100 generally includes a large plurality of ligaments 102 defining open voids (i.e., pores) or channels 104 therebetween. The open voids between ligaments 102 form a matrix of continuous channels 104 having few or no dead ends, such that growth of bone through open porous metal component 100 is substantially uninhibited. Open porous metal component 100 may include up to 75%-85% or more void space therein. Thus, open porous metal component 100 may comprise a lightweight, strong porous structure which is substantially uniform and consistent in composition, and provides a matrix into which bone may grow.

According to some configurations of the instant disclosure, open porous metal component 100 of the orthopaedic implants disclosed herein may comprise at least one exposed porous metal surface 110. As shown in FIG. 1, the terminating ends of ligaments 102, referred to herein as struts 150, define exposed porous metal surface 110. Struts 150, comprising exposed porous metal surface 110, generate a high coefficient of friction when in contact with bone and other tissue. Further, struts 150 impart an enhanced affixation ability to exposed porous metal surface 110, thereby aiding in the initial fixation (upon implantation) of the orthopaedic implant to bone or other tissue.

Open porous metal component 100 may be made of a highly porous biomaterial useful as a bone substitute and/or cell and tissue receptive material. For example, according to embodiments of the instant disclosure, open porous metal component 100 may have a porosity as low as 55%, 65%, or 75% or as high as 80%, 85%, or 90%. An example of open porous metal component 100 is produced using Trabecular Metal™ Technology generally available from Zimmer, Inc., of Warsaw, Ind. Trabecular Metal™ is a trademark of Zimmer, Inc. Such a material may be formed from a reticulated vitreous carbon foam substrate which is infiltrated and coated with a biocompatible metal, such as tantalum, by a chemical vapor deposition ("CVD") process in the manner disclosed in detail in U.S. Pat. No. 5,282,861, entitled OPEN CELL TANTALUM STRUCTURES FOR CANCELLOUS BONE IMPLANTS AND CELL AND TISSUE RECEPTORS, and in Levine, B. R., et al., "Experimental and Clinical Performance of Porous Tantalum in Orthopedic Surgery", Biomaterials 27 (2006) 4671-4681, the disclosures of which are expressly incorporated herein by reference. In addition to tantalum, other metals such as niobium or alloys of tantalum and niobium with one another or with other metals may also be used. Further, other biocompatible metals, such as titanium, a titanium alloy, cobalt chromium, cobalt chromium molybdenum, tantalum, or a tantalum alloy may also be used.

Additionally, embodiments of open porous metal component 100 may comprise a Ti-6Al-4V ELI alloy, such as Tivanium® Alloy which is available from Zimmer, Inc., of Warsaw, Ind. Tivanium® is a registered trademark of Zimmer, Inc. Open porous metal component 100 may also comprise a fiber metal pad or a sintered metal layer, such as a CSTi™, Cancellous-Structured Titanium™ coating or layer, for example. CSTi™ porous layers are manufactured by Zimmer, Inc., of Warsaw, Ind. CSTi™ is a trademark of Zimmer, Inc.

In other embodiments, open porous metal component 100 may comprise an open cell polyurethane foam substrate coated with Ti-6Al-4V alloy using a low temperature arc vapor deposition process. Ti-6Al-4V beads may then be sintered to the surface of the Ti-6Al-4V-coated polyurethane foam substrate. Additionally, another embodiment of open porous metal component 100 may comprise a metal substrate combined with a Ti-6AL-4V powder and a ceramic material, which is sintered under heat and pressure. The ceramic particles may thereafter be removed leaving voids, or pores, in the substrate. Open porous metal component 100 may also comprise a Ti-6Al-4V powder which has been suspended in a liquid and infiltrated and coated on the surface of a polyurethane substrate. The Ti-6Al-4V coating may then be sintered to form a porous metal structure mimicking the polyurethane foam substrate. Further, another embodiment of open porous metal component 100 may comprise a porous metal substrate having particles, comprising altered geometries, which are sintered to a plurality of outer layers of the metal substrate.

Additionally, open porous metal component 100 may be fabricated according to electron beam melting (EBM) and/or laser engineered net shaping (LENS). For example, with EBM, metallic layers (comprising one or more of the biomaterials, alloys, and substrates disclosed herein) may be coated (layer by layer) on an open cell substrate using an electron beam in a vacuum. Similarly, with LENS, metallic powder (such as a titanium powder, for example) may be deposited and coated on an open cell substrate by creating a molten pool (from a metallic powder) using a focused, high-powered laser beam.

Open porous metal component 100 may also be fabricated such that it comprises a variety of densities in order to selectively tailor the structure for particular applications. In particular, as discussed in the above-incorporated U.S. Pat. No. 5,282,861, open porous metal component 100 may be fabricated to virtually any desired density, porosity, and pore size (e.g., pore diameter), and can thus be matched with the surrounding natural tissue in order to provide an improved matrix for tissue ingrowth and mineralization.

2. Bone Growth Promoting Agents for Use in Combination with Open Porous Metal Component.

Figure 2:
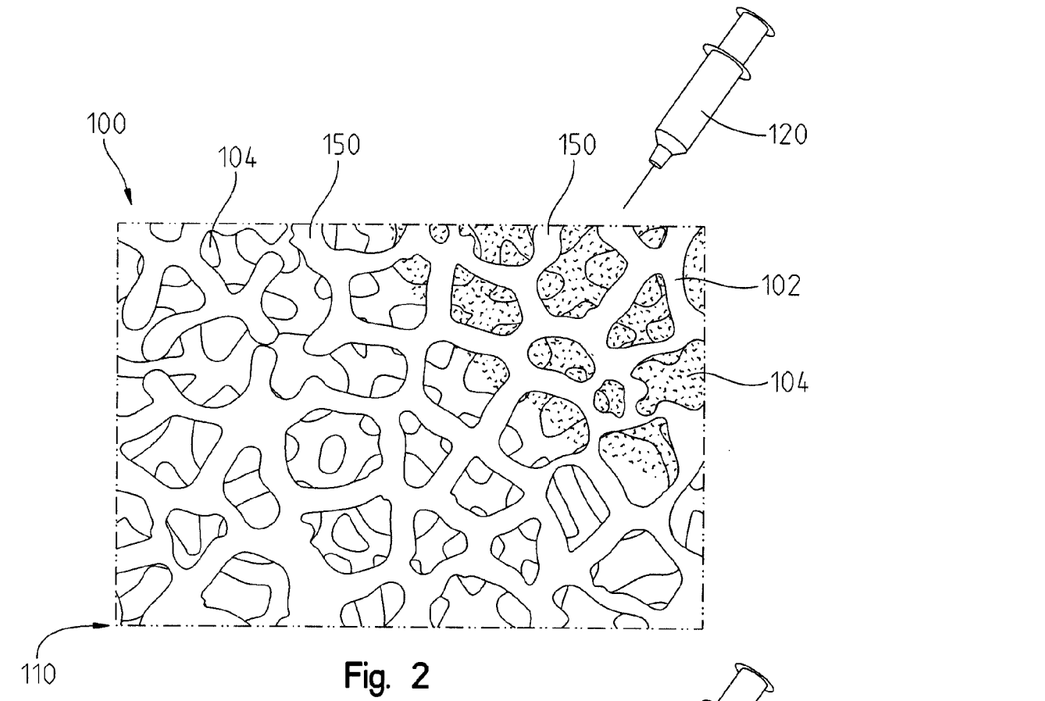
FIG. 2 is an enlarged cross-sectional view of the open porous metal component of FIG. 1 being combined with one or more bone growth factors.
Figure 4:
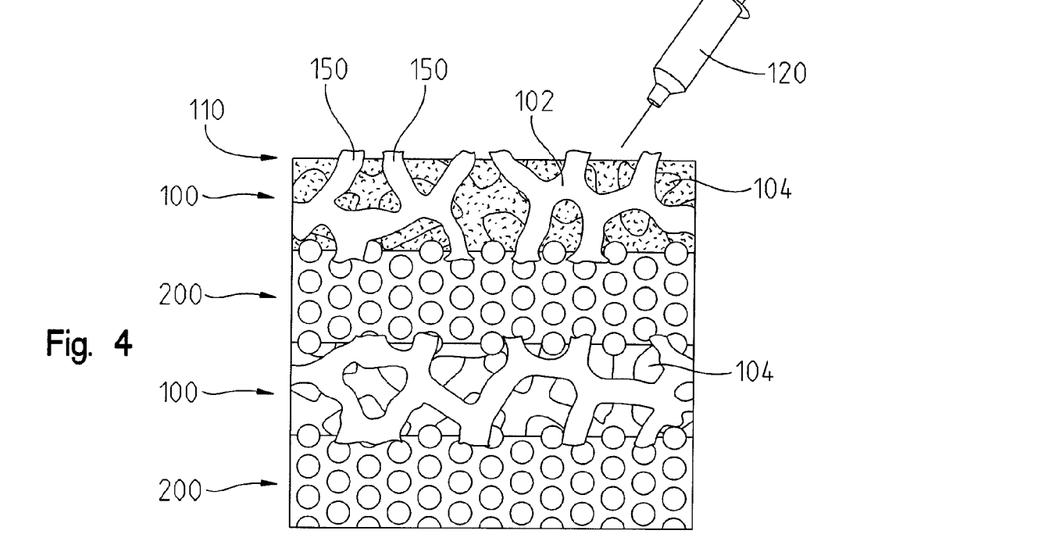
FIG. 4 is a cross-sectional view showing the orthopaedic implant of FIG. 3 being combined with one or more bone growth factors.

In addition to comprising selectively tailored densities, porosities, and pore sizes, open porous metal component 100 of the orthopaedic implants disclosed herein may also be combined with various bone growth factors or agents. Referring to FIGS. 2 and 4, one or more bone growth factors or agents may be injected into channels 104 (FIG. 1), with syringe 120 for example, or applied to one or more exposed porous metal surfaces 110 of open porous metal component 100. As shown, in some configurations open porous metal component 100 may be combined with one or more growth factors or agents such that the growth factors or agents partially fill open porous metal component 100. In other configurations, growth factors and agents may substantially fill channels 104 throughout the dimensional extent of open porous metal component 100. According to embodiments of the instant disclosure in which the dimensional extent of open porous metal component 100 is substantially filled, as low as 35%, 40%, or 45% or as high as 85%, 90%, or 95%, or more, of the volume within channels 104 of open porous metal component 100 may be filled with growth factors or agents.

Bone growth factors or agents which may be combined with the orthopaedic implants disclosed herein include growth factors influencing the attraction, proliferation, differentiation, and organization of all bone cells types such as osteocytes, osteoclasts, osteoblasts, odentoblasts, cementoblasts, and precursors thereof (e.g., stem cells). Additionally, the bone growth factors or agents disclosed herein include growth factors influencing the attraction, proliferation, differentiation, and organization of soft tissue cell types such as fibrocytes, chondrocytes, tenocytes, ligament cells, and precursors thereof (e.g., stem cells). Further, the bone growth factors disclosed herein also include angiogenic factors, such as vascular endothelial growth factor (VEGF) for example.

According to the instant disclosure, exemplary bone growth factors or agents include, but are not limited to, bone morphogenic proteins (BMP) such as BMP-1, BMP-2, BMP-3, BMP-4, BMP-5, BMP-6, BMP-7, transforming growth factor (TGF)-β, platelet drived growth factors, and epidermal growth factor, for example. Other exemplary bone growth factors or agents which may be combined with the orthopaedic implants disclosed herein include bone proteins, such as osteocalcin, osteonectin, bone sialoprotein, lysyloxidase, cathepsin L, biglycan, fibronextin fibroblast growth factor (FGF), platelet derived growth factor, calcium carbonate, and thrombospondin (TSP). Additionally, exemplary growth factors or agents which may be combined with the orthopaedic implants disclosed herein may also include fibroblast growth factors (FGF) such as FGF-I, FGF-II, FGF-9, insulin growth factor (IGF)-I, IGF-II, platelet derived growth factor, epithelial growth factors (EGF), and TGF-α. In addition to the bone growth factors described above, the orthopaedic implants disclosed herein may also be combined with other general cellular growth factors and with pluripotent cells as well as chondrocytes, in order to further support regeneration of bony tissue within the bone voids and throughout the orthopaedic implants. In some embodiments, in addition to or as an alternative to the other exemplary agents and growth factors described herein, strontium may be combined with the disclosed orthopedic implants as an active agent to promote bone growth.

Exemplary combinations or mixtures of bone growth factors and agents, which may be combined with open porous metal component 100 of the orthopaedic implants disclosed herein, may include the mixtures described in U.S. Patent Publication No. 2011/0165199, entitled COMPOSITION AND PROCESS FOR BONE GROWTH AND REPAIR, the entire disclosure of which is hereby incorporated by reference. In other configurations, open porous metal component 100 may be combined with the mixtures of bone growth factors and agents described in U.S. Pat. No. 7,718,616, entitled BONE GROWTH PARTICLES AND OSTEOINDUCTIVE COMPOSITION THEREOF, the entire disclosure of which is hereby incorporated by reference. Still other mixtures of bone growth factors and agents which may be combined with open porous metal component 100 include those mixtures described in U.S. Pat. No. 5,290,763, entitled OSTEOINDUCTIVE PROTEIN MIX- TURES AND PURIFICATION PROCESSES, the entire disclosure of which is hereby incorporated by reference.

Prior to combining the bone growth factors or agents, and mixtures thereof, with open porous metal component 100, the growth factors and agents may first be combined with, or dissolved within, a suitable carrier such as a calcium carrier, a phosphate carrier, a ceramic carrier, or a polylactide co-glycolide (PLGA) carrier. An example of one such carrier, as described in greater detail below, includes resorbable bone growth promoting component 200. For example, one or more bone growth factors or agents may be combined (e.g., mixed with or dissolved in) resorbable bone growth promoting component 200, then inserted into channels 104, or coated on one or more exposed porous metal surfaces 110, of open porous metal component 100.

Although open porous metal component 100 of the orthopaedic implants disclosed herein may comprise substantially uniform porosity, density, and/or void (pore) size throughout, some configurations may comprise open porous metal component 100 having at least one of pore size, porosity, and/or density being varied as described in U.S. Provisional Patent Application Ser. No. 61/561,475 entitled POROUS METAL DEVICE FOR REGENERATING SOFT TISSUE-TO-BONE INTERFACE filed on Nov. 18, 2011. For example, with reference to FIG. 3 which depicts an illustrative orthopaedic implant comprising alternating layers of open porous metal component 100', 100" stacked (or layered) between alternating layers of resorbable bone growth promoting component 200', 200", the pore size and/or porosity of the first layer of open porous metal component 100' may vary from the pore size and/or porosity of the second layer of open porous metal component 100". Additionally, in some configurations the pore size and/or porosity within a same layer of open porous metal component 100 may vary. The ability to selectively tailor the structural properties of open porous metal component 100 as described herein, enables the orthopaedic implants of the present disclosure to better distribute stress loads throughout the surrounding tissue and promote specific tissue type ingrowth within channels 104 (FIG. 1) of open porous metal component 100.

Figure 3:
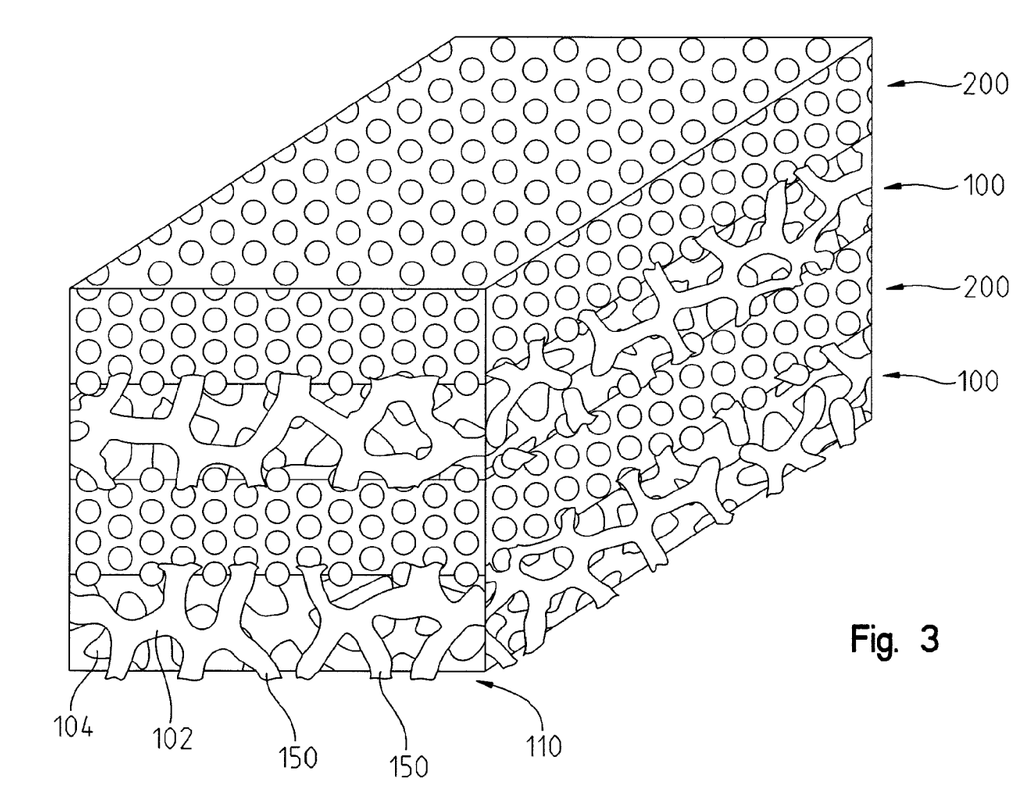
FIG. 3 is a perspective view illustrating an embodiment of an orthopaedic implant according to the present disclosure comprising individual layers of the open porous metal component stacked between individual layers of the resorbable bone growth promoting component.

Referring to FIG. 3, open porous metal component 100 may comprise one or more porous metallic sheets, the sheets being relatively thin (e.g., having a thickness of as low as two pore diameters to as high as twelve or more pore diameters) and being at least partially flexible. Such configurations allow open porous metal component 100 to be shaped and sized according to a particular application. For example, a surgeon may shape, cut, bend, or trim open porous metal component 100 to any desired custom size and/or shape in order to meet a patient's particular need. As such, open porous metal component 100 advantageously enables a surgeon to utilize the orthopaedic implants disclosed herein to fill unique bone voids having different shapes and sizes and occurring at various locations.

Resorbable Bone Growth Promoting Component.

Referring to FIG. 3, the orthopaedic implants disclosed herein comprise, in part, resorbable bone growth promoting component 200. According to embodiments of the orthopaedic implants disclosed herein, resorbable bone growth promoting component 200 may comprise a solid mass, such as a powder (loose or compressed), or a soft mass, such as a putty or paste. Further, resorbable bone growth promoting component 200 comprises an osteoconductive carrier, capable of providing one or more bone growth factors for aiding the bone regeneration process.

As described herein, resorbable bone growth promoting component 200 provides a temporary matrix for cell proliferation and extracellular-matrix deposition with consequent bone ingrowth until new bony tissue regenerates. As explained in the above-incorporated U.S. Pat. No. 7,718,616, during bone regeneration resorbable bone growth promoting component 200 is resorbed or incorporated into the newly formed bone. Resorbable bone growth promoting component 200 also provides a template for vascularization of new bony tissue, and may actively participate in the regenerative process through the release of growth differentiation factors. Additionally, the structural properties of resorbable bone growth promoting component 200 influence the survival, signaling, growth, propagation, and reorganization of cells.

Embodiments of resorbable bone growth promoting component 200 may comprise CopiOs® Bone Void Filler which is available from Zimmer, Inc., of Warsaw, Ind., for example. CopiOs® is a registered trademark of Zimmer, Inc. Resorbable bone growth promoting component 200 may comprise a fibrillar collagen as described in detail in the above-incorporated U.S. Pat. No. 7,718,616. Fibrillar collagen comprising resorbable bone growth promoting component 200 may be obtained from native sources such as human or animal dermis, tendon, cartilage or bone, and may be recovered through proteolytic degradation of collagen fiber crosslinks as detailed in U.S. Pat. No. 7,718,616. Further, during the manufacture of fibrillar collagen, potential antigenic portions of the collagen molecule may be removed, resulting in a product that is highly biocompatible and well-tolerated by host tissue. In such configurations, resorbable bone growth promoting component 200 provides a physical and chemical milieu favorable to bone regeneration by providing a favorable extracellular matrix for bone forming cells (e.g., osteoblasts, osteoclasts, osteocytes, etc.).

Additionally, configurations of resorbable bone growth promoting component 200 may comprise a compound which renders it acidic. An example of such a configuration is described in the above-incorporated U.S. Patent Publication No. 2011/0165199 which describes a configuration of resorbable bone growth promoting component 200 comprising a porous collagen with a calcium source and/or a phosphate source embedded therein. Such configurations of resorbable bone growth promoting component 200 provide a structure for the growth of bone and an acidic environment for enhancing the activity of bone growth proteins, thereby inducing and further enhancing the production of bone.

According to the instant disclosure, resorbable bone growth promoting component 200 may comprise various other compositions. For example, resorbable bone growth promoting component 200 may comprise a porous collagen mix (e.g., type I collagen) having blood and/or bone fragments embedded therein. Other embodiments of resorbable bone growth promoting component 200 may comprise a synthetic hydroxylapatite mixture with an external negative charge. Still, other embodiments of resorbable bone growth promoting component 200, within the scope of the present disclosure, may include a resorbable inorganic calcium phosphate composition having human fibrin embedded therein. Even further configurations of resorbable bone growth promoting component 200 may comprise a synthetic biocompatible sulfate composition.

Referring to FIG. 3, an embodiment of resorbable bone growth promoting component 200 is shown as a solid mass (a compressed powder). The configuration of resorbable bone growth promoting component 200 shown in FIG. 3 includes two discs or sheets, stacked between two layers or sheets of open porous metal component 100. Resorbable bone growth promoting component 200 comprises an open pore, fully interconnected three-dimensional geometry which allows bone ingrowth. In addition to allowing bone ingrowth, such configurations of resorbable bone growth promoting component 200 also facilitate vascularization and allow for the diffusion of nutrients, gases, and metabolic waste during the bone regeneration process.

Although depicted in FIG. 3 as comprising a solid mass (a compressed powder in the form of two discs), resorbable bone growth promoting component 200 may also comprise a soft mass, such as a sponge or putty consistency (having a physical consistency between a liquid and a solid). Resorbable bone growth promoting component 200 may also take the form of a loose (non-compressed) powder which, as is described herein, may be hydrated into a soft mass, or may be hydrated to have a more liquid-like consistency. When in the form of a soft mass, resorbable bone growth promoting component 200 may be molded to a desired shape and size, and in some cases may be partially or substantially disposed within channels 104 (FIG. 1) of open porous metal component 100.

As described in the above-incorporated U.S. Pat. No. 7,718,616, configurations of resorbable bone growth promoting component 200 may have a total pore volume which is similar to cancellous bone. Cancellous bone is a highly porous structure (having a pore volume from as low as approximately 50 volume % to as high as approximately 97 volume %) arranged in a sponge-like form, with pore diameters ranging from as low as 1 µm to as high as approximately 1000 µm. Thus, according to configurations of the orthopaedic implants disclosed herein, resorbable bone growth promoting component 200 may comprise a total pore volume as low as 50, 55, or 60% to as high as 80, 90, or 97% or any value there between. Further, resorbable bone growth promoting component 200 may comprise pore diameters as small as approximately 0.5, 1, or 2, to as high as 800, 900, or 1000 µm, or any value there between.

Further, resorbable bone growth promoting component 200 also comprises an osteoconductive carrier for one or more bone growth factors or agents as detailed in the above-incorporated U.S. Pat. No. 7,718,616. For example, with reference to FIG. 4, syringe 120 may be utilized to inject one or more bone growth factors or agents within channels 104 of open porous metal component 100. In some configurations, the growth factors and agents will reach resorbable bone growth promoting component 200, where they are wicked or absorbed by resorbable bone growth promoting component 200. Resorbable bone growth promoting component 200 of some configurations of the orthopaedic implant described herein may wick (or absorb) greater than seven times its weight. Additionally, upon wicking the growth factors or agents, the form of resorbable bone growth promoting component 200 may be altered (e.g., change from a solid mass to a soft mass). Further, although bone growth factors or agents are shown in FIG. 4 being injected into the orthopaedic implant it should be understood that the orthopaedic implant may be dipped or soaked into a mixture of bone growth factors or agents as well.

As disclosed in the above-incorporated U.S. Pat. No. 7,718,616, the composition and the physical characteristics of resorbable bone growth promoting component 200 may affect the rate of elution of the growth factors and other agents combined with the resorbable bone growth promoting component 200. For example, as explained in U.S. Pat. No. 7,718,616, cross-linking of materials (e.g., collagen) comprising resorbable bone growth promoting component 200, the pore size, and the porosity of resorbable bone growth promoting component 200 may all affect the release of growth factors or agents combined therewith.

Additionally, according to some configurations, a polymer-based and/or a receptor-based system may be utilized in conjunction with resorbable bone growth promoting component 200 for controlling the rate of elution and localization of the growth factors and other agents. For example, the growth factors or agents combined with resorbable bone growth promoting component 200 may be encapsulated within a polymer-based coating, or combined with a polymer-based matrix, before being combined with the resorbable bone growth promoting component 200. Similarly, a ligand (such as a protein, antibody, or portion thereof, for example) may be attached to the growth factor or agent as well. As such, in addition to the physical characteristics of resorbable bone growth promoting component 200, release of the growth factors or agents from a polymer-based coating (or matrix), and/or targeting of a ligand (attached to the growth factors or agents), may also affect the rate of elution and localization of the growth factors and agents from resorbable bone growth promoting component 200.

In addition to the exemplary growth factors and agents already described herein, resorbable bone growth promoting component 200 may also be combined with the mixtures of various bone growth factors or agents, such as described in U.S. Patent Publication No. 2011/0165199, for example. Additionally, in some configurations, resorbable bone growth promoting component 200 may be combined with the mixtures of various bone growth factors or agents described in U.S. Pat. No. 7,718,616. Other mixtures of bone growth factors or agents which may be combined with resorbable bone growth promoting component 200 include those mixtures described in U.S. Pat. No. 5,290,763.

Additionally, in some configurations of the orthopaedic implants described herein, resorbable bone growth promoting component 200 may be combined with biological fluids such as bone marrow aspirates. As explained in U.S. Pat. No. 7,718,616, bone marrow aspirates contain osteoinductive agents such as mesenchymal stem cells which are multipotent cells capable of differentiating along several lineage pathways to aid in the production of bone. Other exemplary biological fluids which may be combined with resorbable bone growth promoting component 200 include blood, plasma, serum, and bone marrow. In addition to biological fluids, resorbable bone growth promoting component 200 may also be combined with a buffer, such a buffer capable of buffering to the physiological pH values of human serum (pH 7.1 to pH 7.4), for example.

Further, in some configurations resorbable bone growth promoting component 200 may also be combined with osteoinductive bone components including demineralized bone and autologous bone. As explained in U.S. Pat. No. 7,718,616, demineralization may be performed, for example, by exposing powdered bone (from any human or mammalian source) to acidic solutions (i.e., HCl, acetic acid, ethylene diamine tetracetic acid) with a pH less than about 4. Further, bone which has not been demineralized may also be included in resorbable bone growth promoting component 200.

Even further, in addition to the liquid compositions already disclosed herein, resorbable bone growth promoting component 200 may also be combined with natural and/or synthetic polymers such as described in the above-incorporated U.S. Patent Publication No. 2011/0165199. Exemplary natural and synthetic polymers which may be combined with resorbable bone growth promoting composition 200 include aliphatic polyesters, polyethylene glycols, polyanhydrides, dextran polymers, and/or polymeric orthophosphates.

As discussed in greater below, the orthopaedic implants disclosed herein may have various configurations. Additionally, open porous metal component 100 and resorbable bone growth promoting component 200, comprising the orthopaedic implants described herein, may have various dimensions. For example, in configurations of the orthopaedic implants comprising layers, each layer of open porous metal component 100 may comprise a thickness of as low as approximately 1, 2, or 3 mm, to as high as approximately 6, 7, or 8 mm. Likewise, each layer of resorbable bone growth promoting component 200 may also comprise a thickness of as low as approximately 1, 2, or 3 mm, to as high as approximately 6, 7, or 8 mm, for example. Further, the orthopaedic implants describe herein may be dimensioned such that, when implanted, the orthopaedic implants may fill a critical size bone void (for example, a void of greater than 7 mm), and new bone will grow throughout all layers comprising the orthopaedic implant.

Exemplary Bone Void Implant Embodiments of Orthopaedic Implants

Figure 5A:
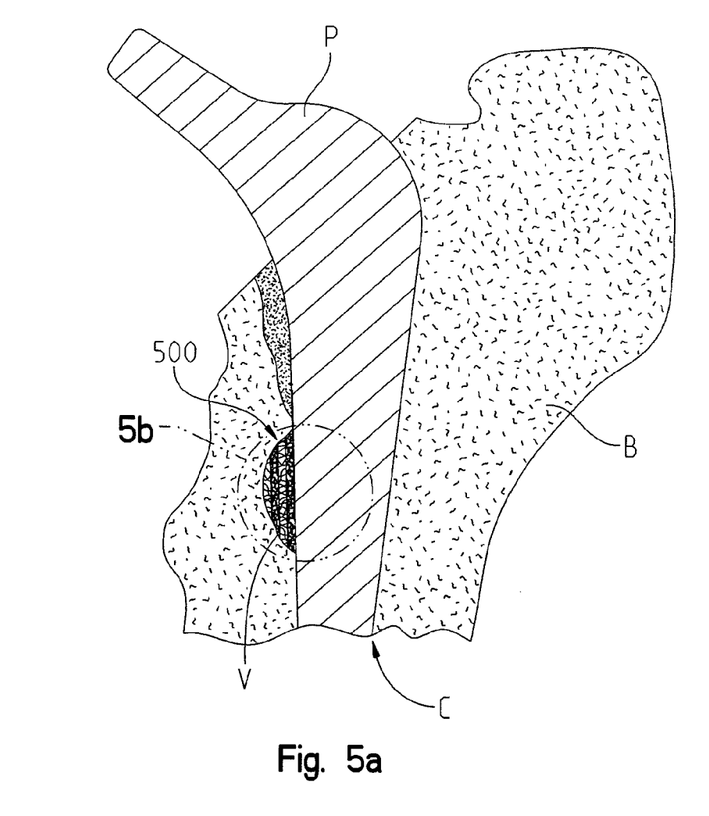
FIG. 5a is a cross-sectional view illustrating an orthopaedic implant according to the present disclosure implanted within a void in a femur.
Figures 6A, 6B:
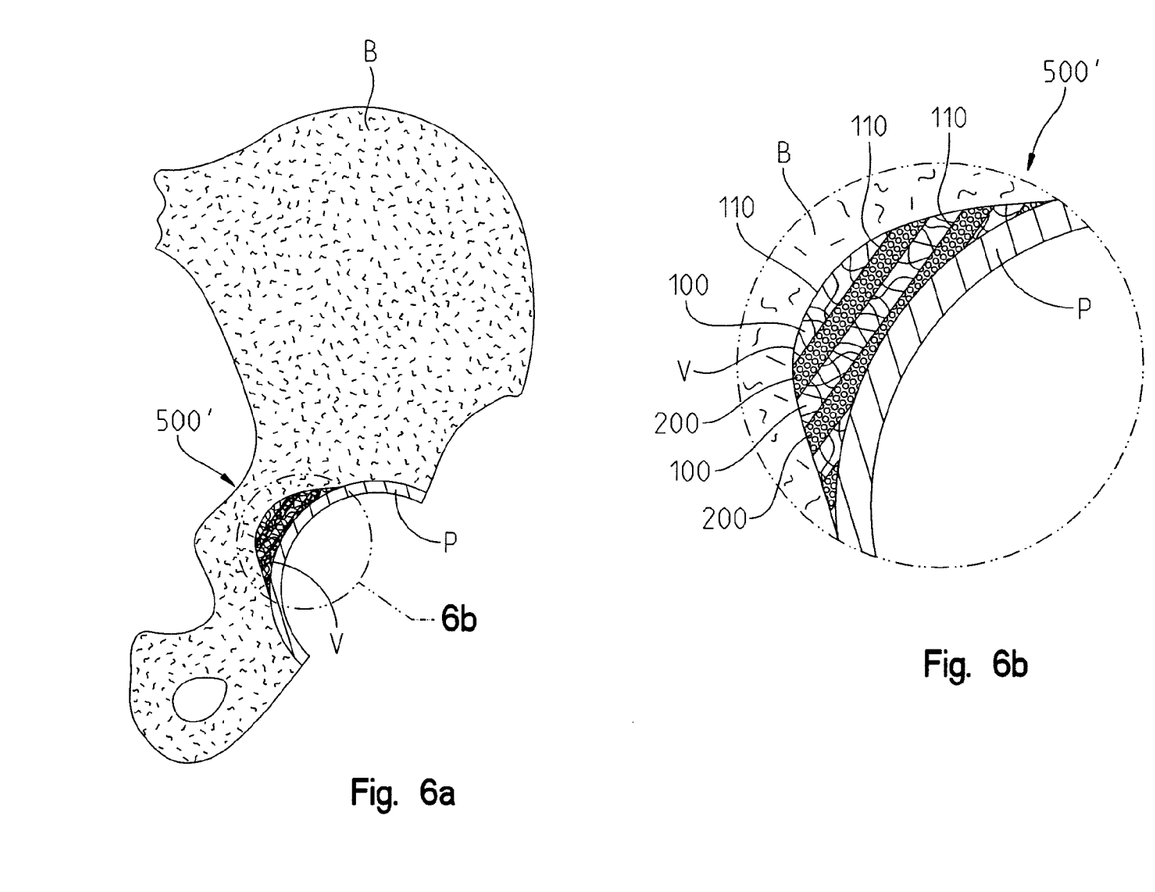

Referring to FIGS. 5a and 6a, illustrative embodiments of orthopaedic implant 500, 500' being used to fill a void V in a bone B are shown. As depicted, orthopaedic implant 500 may fill a void V in a bone B prior to implantation of a prosthesis P within bone B. Further, the configurations of orthopaedic implant 500, 500' shown in FIGS. 5a and 6a include open porous metal component 100 and resorbable bone growth promoting component 200 both comprising multiple, alternating layers, such as shown in FIG. 3.

Figure 5B:
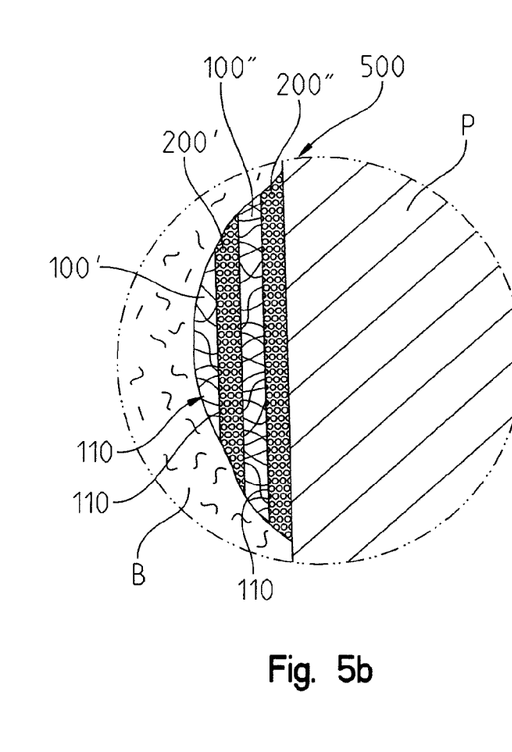

Referring to FIGS. 5a and 5b, orthopaedic implant 500 is shown filling void V adjacent canal C in proximal femur bone B. As shown, orthopaedic implant 500 comprises a first layer of open porous metal component 100' having a first layer of resorbable bone growth promoting component 200' stacked or layered thereon. Orthopaedic implant 500 also include a second layer of open porous metal component 100" layered on the first layer of resorbable bone growth promoting component 200', and a second layer of resorbable bone growth promoting component 200" layered on the second layer of open porous metal component 100".

With reference to FIG. 5b, orthopaedic implant 500 is configured to completely fill void V, within bone B, adjacent prosthesis P. Further orthopaedic implant 500 may be orientated in void V such that exposed porous surface 110 of open porous metal component 100' contacts bone B outlining void V. As described in detail above, struts 150 comprising exposed porous surface 110 of open porous metal component 100' provide a coefficient of friction which aides in providing initial fixation of orthopaedic implant 500 to bone B. Further, exposed porous surface 110 allows for ingrowth of bone in the plurality of pores 104.

While orthopaedic implant 500 is depicted as having open porous metal component 100' contacting bone B outlining void V, and resorbable bone growth promoting component 200" contacting prosthesis P, various configurations of the layers comprising orthopaedic implant 500 are possible. Additionally, in some configurations orthopaedic implant 500, may include one or more additional layers, such as a bone cement layer, which contacts prosthesis P and provides initial fixation between orthopaedic implant 500 and prosthesis P. Further embodiments of orthopaedic implant 500 are possible in which prosthesis P may also comprise an open porous metal, thereby allowing for fixation of orthopaedic implant 500 to prosthesis P, by way of regenerated bone.

Referring to FIGS. 6a and 6b, a configuration of orthopaedic implant 500' being used to fill void V in an acetabulum bone B is depicted. As shown, orthopaedic implant 500' may be used to fill a void V in a bone B prior to affixation of acetabular cup prosthesis P to bone B.

The configuration of orthopaedic implant 500' depicted in FIGS. 6a and 6b comprises three layers of each of open porous metal component 100 and resorbable bone growth promoting component 200, arranged in multiple, alternating layers (similar to the configuration of orthopaedic implant 500 depicted in FIGS. 5a and 5b). As shown in FIGS. 6a and 6b, orthopaedic implant 500' has been shaped to completely fill void V, within bone B, adjacent prosthesis P. For example, as can be seen in FIGS. 6a and 6b, layers of orthopaedic implant 500' adjacent prosthesis P may be reamed or trimmed to create an aperture therein such that orthopaedic implant 500' completely fills void V.

Similar to configurations of orthopaedic implant 500, shown in FIG. 5b, FIG. 6b depicts orthopaedic implant 500' being orientated in void V such that exposed porous surface 110 of open porous metal component 100 contacts bone B outlining void V. While depicted as having a layer of open porous metal component 100 contacting bone B, configurations of orthopaedic implant 500' may have resorbable bone growth component contacting bone B. Additionally, embodiments of orthopaedic implant 500' may also include an additional layer such as bone cement contacting prosthesis P and spacing (at least partially) orthopaedic implant 500' from the prosthesis P. Further, as with orthopaedic implant 500, in some configurations prosthesis P comprises an open porous metal, thereby allowing for fixation of orthopaedic implant 500' to prosthesis P, by way of regenerated bone.

Referring again to both FIGS. 5a and 6a, the illustrated configurations of orthopaedic implant 500, 500' may be combined with various bone growth factors or agents, as discussed herein. For example, a configuration of orthopaedic implant 500 may include a mixture of one or more bone growth factors coated along one or more exposed porous surface 110 of one or more layer of open porous metal component 100. Additionally, configurations of orthopaedic implant 500, 500' may include one or more bone growth factors disposed within channels 104 of one or more layers of open porous metal component 100. Further, as disclosed herein, in some configurations one or more layers of resorbable bone growth promoting component 200 may also be combined with one or more bone growth factors or agents.

While resorbable bone growth promoting component 200 is shown as a solid mass (compressed powder), configurations of orthopaedic implant 500, 500' may comprise resorbable bone growth promoting component 200 in the form of a soft mass, such as a sponge, paste, or putty, for example. Also, in addition to separating (or spacing) the individual layers of open porous metal component 100 (e.g., layers 100' and 100" shown in FIG. 5b), one or more of the layers of resorbable bone growth promoting component 200 may also be partially disposed within at least a portion of one or more exposed porous surfaces 110 of open porous metal component 100 (such as shown in FIG. 4).

In use, the configurations of orthopaedic implant 500, 500' shown in FIGS. 5b and 6b, may be shaped and sized according to a particular application. For example, a surgeon may shape, cut, bend, or trim one or more of the layers of open porous metal 100 and/or resorbable bone growth promoting component 200 to any desired custom size and shape in order to meet a particular need. Shaping and sizing of open porous metal component 100 and resorbable bone growth promoting component 200 may occur prior to, or after, arranging orthopaedic implant 500, 500' in the layered or stacked configuration depicted in FIGS. 5b and 6b, for example. As such, orthopaedic implant 500, 500' may be used to fill unique bone voids having different shapes and sizes and occurring at various patient specific locations.

Additionally, when implanted, the configurations of orthopaedic implant 500, 500' shown in FIGS. 5a and 6a promote new bone regeneration, while providing initial structural support and fixation within void V. As detailed above, resorbable bone growth promoting component 200 provides a temporary matrix for cell proliferation and extracellular matrix deposition, which also promotes vascularization for supporting continued bone regeneration and maintenance. As new bone is regenerated, resorbable bone growth promoting component 200 is resorbed into the new bone. Further, also detailed above, resorbable bone growth promoting component 200 may also act as a carrier for providing various osteogenic growth factors and agents thereby aiding in the induction of new bone growth.

During regeneration of new bone, open porous metal component 100 provides a matrix which supports bone ingrowth and mineralization therein as well as providing structural support to orthopaedic implant 500, 500' and bone B. Upon bone ingrowth within open porous metal component 100, a rigid and secure secondary fixation of orthopaedic implant 500, 500' within bone is provided.

While configurations of orthopaedic implant 500, 500' disclosed herein have been described and depicted in use for filling a void V, adjacent a prosthesis, in a femur and acetabulum, configurations of orthopaedic implant 500, 500' may be used for filling voids in other bones and voids not adjacent to a prosthesis. Additionally, although the configurations of orthopaedic implant 500, 500' depicted herein comprise only two or three layers, configurations of orthopaedic implant 500 may include additional layers of either, or both, of open porous metal component 100 and resorbable bone growth promoting component 200.

Exemplary Augment Embodiments of Orthopaedic Implants

Figure 7:
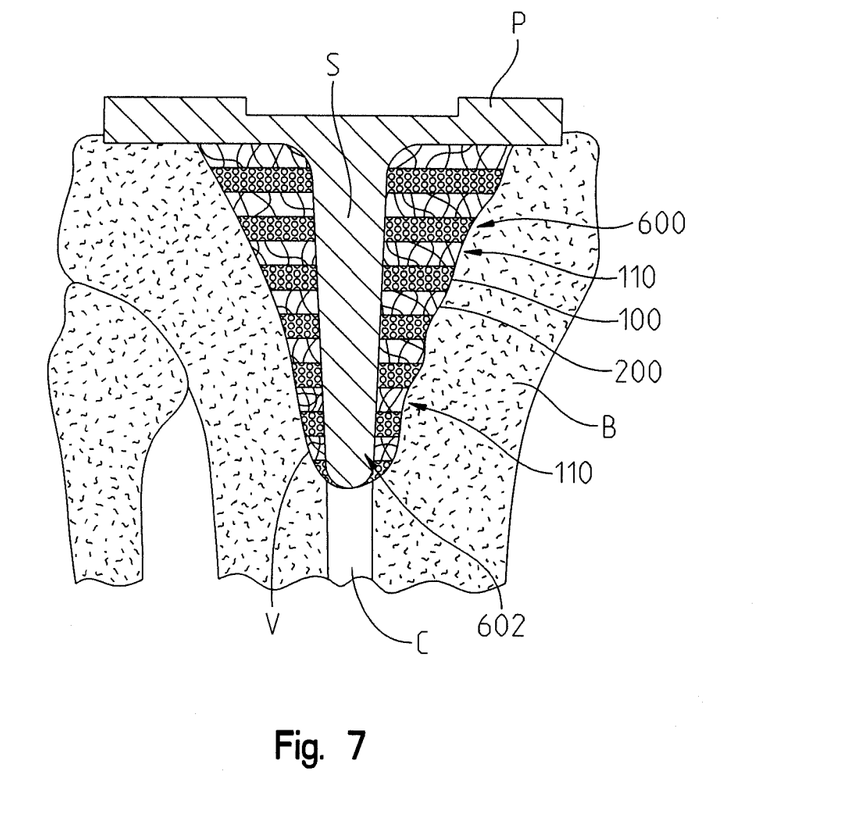
FIG. 7 is a cross-sectional view of another embodiment of an orthopaedic implant according to the present disclosure comprising an augment or support structure for a tibial baseplate implanted within the intramedullary canal of a tibia.
Figure 8:
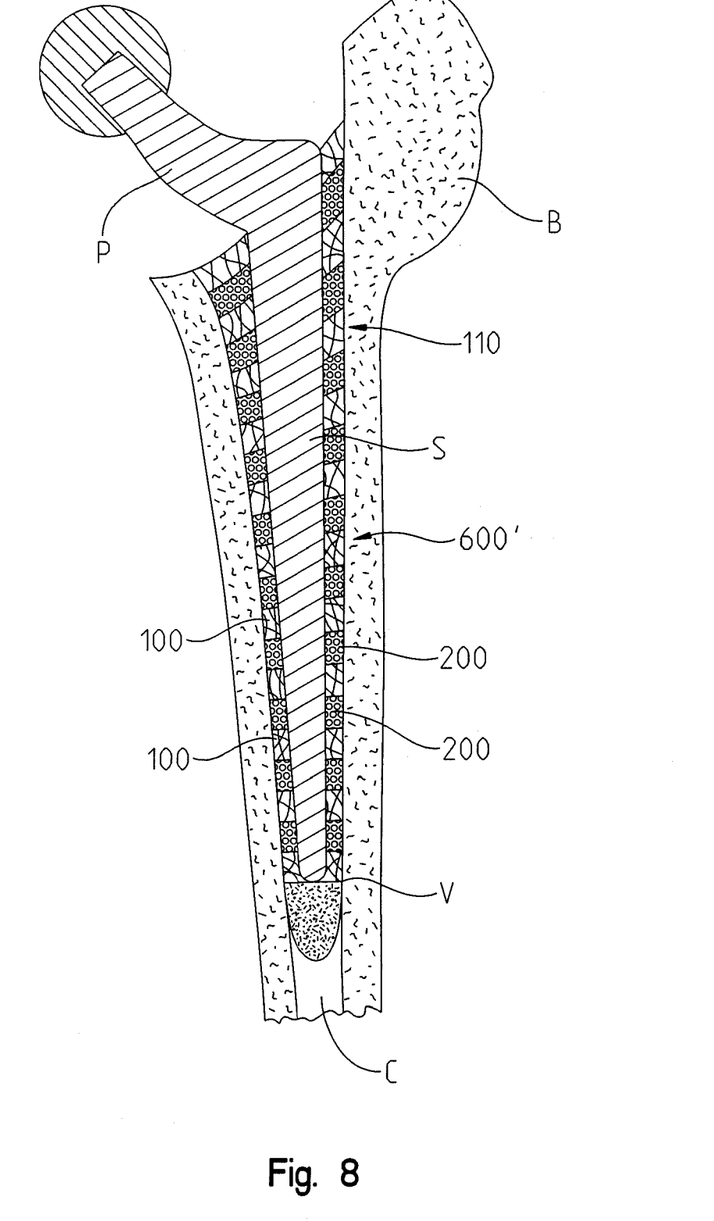
FIG. 8 is a cross-sectional view of yet another embodiment of an orthopaedic implant according to the present disclosure comprising an augment or support structure for a femoral prosthesis implanted within the femoral canal of a femur.
Figure 9A:
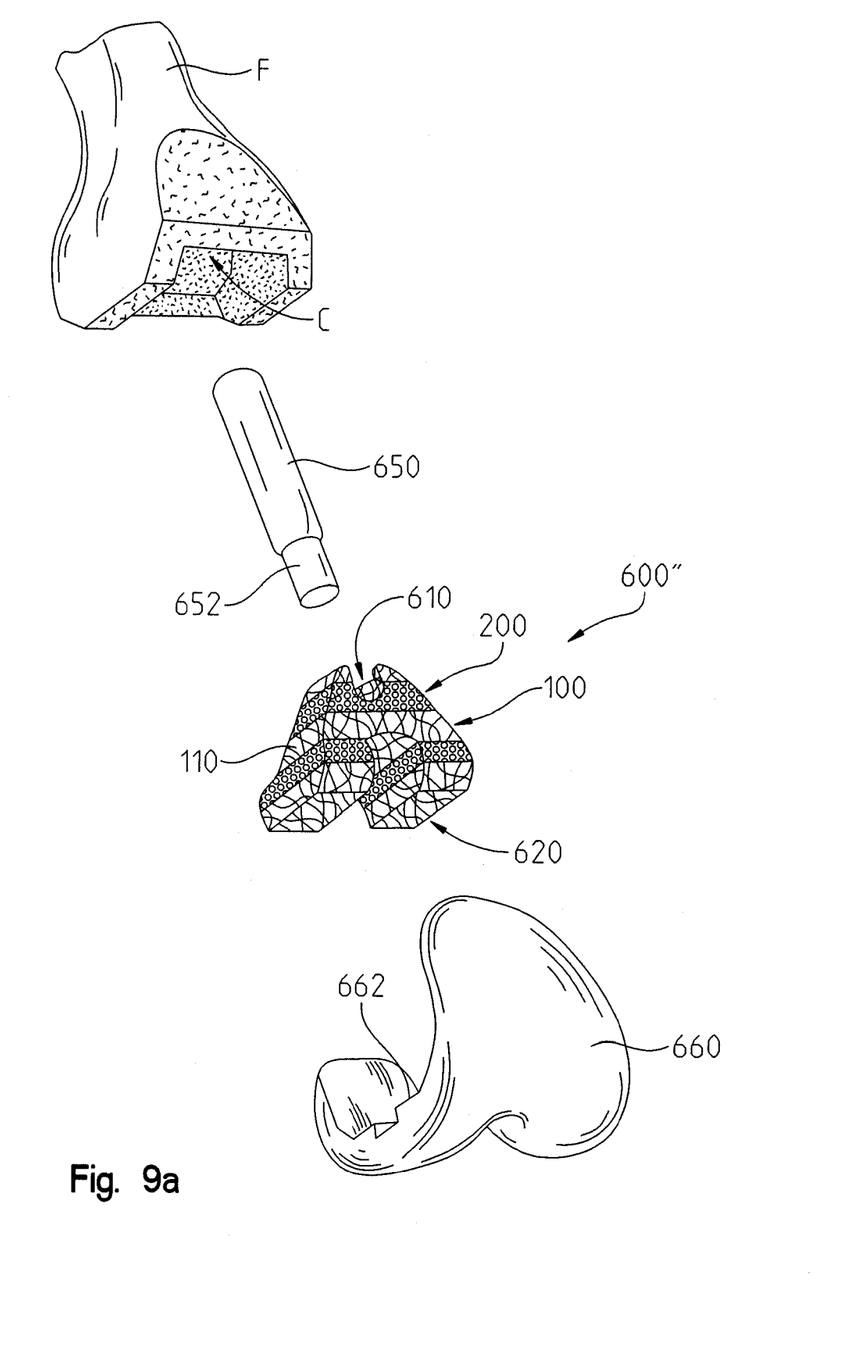
FIG. 9a is a perspective view of another embodiment of an orthopaedic implant according to the present disclosure for use with a distal femoral prosthesis.

Referring to FIGS. 7, 8, and 9a exemplary embodiments of orthopaedic implant 600, 600', 600" are depicted for providing a support structure, or augment, for use with various prosthetic implants. As shown in FIGS. 7, 8, and 9a, the configurations of orthopaedic implant 600, 600', 600" comprise multiple layers of each of open porous metal component 100, and resorbable bone growth promoting component 200, arranged in alternating layers.

The multiple layers of open porous metal component 100 and resorbable bone growth promoting component 200 comprising the configurations of orthopaedic implant 600, 600', 600" shown in FIGS. 7, 8, and 9a are arranged such that orthopaedic implant 600, 600', 600" fills the void V between the bone B and the prosthesis P, and such that orthopaedic implant 600, 600', 600" contacts both bone B and prosthesis P. Advantageously, orthopaedic implant 600, 600', 600" provides a stable support (or augment) structure for prosthetic implants, and promotes bone regeneration around and, in some configurations, within the prosthetic implants.

Referring to FIG. 7, orthopaedic implant 600 is depicted as filling a void V within the intramedullary canal C, and supporting a tibial baseplate prosthesis P having stem S. As shown in FIG. 7, orthopaedic implant 600 defines bore 602, allowing stem S of prosthesis P to be inserted therein. Also, as shown orthopaedic implant 600 may be orientated in void V such that portions of exposed porous surface 110 of some or all of the layers of open porous metal 100 contact bone B, thereby providing initial fixation for orthopaedic implant 600 within void V.

Additionally, as discussed herein, configurations of orthopaedic implant 600 may be combined with various bone growth factors or agents such as discussed herein. For example, one or more bone growth factors and/or agents can be injected or inserted into channels 104 of one or more layers of open porous metal component 100 comprising orthopaedic implant 600. Further, one or more growth factors and/or agents may be coated on one or more exposed porous surface 110 of the one or more layers of open porous metal 100.

Also, as discussed in detail above, one or more layer of resorbable bone growth promoting component 200 may be combined with one or more growth factors and/or agents. While resorbable bone growth promoting component 200 is depicted as a solid mass (compressed powder), orthopaedic implant 600 may include one or more layers of resorbable bone growth promoting component 200 comprising a soft mass. Further, resorbable bone growth promoting component 200 may also be partially disposed within at least a portion of open porous metal component 100, such as illustrated in FIGS. 3 and 4.

In some configurations, stem S of tibial baseplate prosthesis P may also comprise open porous metal 100. According to such configurations, regenerated bone may provide a secondary fixation of orthopaedic implant 600 to stem S, thereby providing more natural and rigid support for prosthesis P and aiding in preventing degradation of bone adjacent orthopaedic implant 600 and prosthesis P.

Advantageously, during implantation, orthopaedic implant 600 may be shaped and sized according to a particular need. For example, a surgeon may cut, trim, ream, and bend one or more layers of either or both of resorbable bone growth promoting component 200 and open porous metal component 100. Shaping and sizing of orthopaedic implant 600 may occur prior to or after assembling orthopaedic implant 600. A surgeon may also insert orthopaedic implant 600 into canal C, and thereafter prepare bore 602. As such, orthopaedic implant 600 may be used in place of standard-sized augments, thereby providing a customizable option for supporting prosthetic implants which also promotes the regeneration of natural bone surrounding prosthesis P.

Referring to FIG. 8, another configuration of orthopaedic implant 600' is depicted, filling a void V within femoral canal C and supporting a femoral prosthesis P having stem S. As shown in FIG. 8, orthopaedic implant 600" also defines bore 602', allowing stem S of prosthesis P to be inserted therein. Also, similar to FIG. 7, orthopaedic implant 600' is orientated within void V such that portions of exposed porous surface 110 of some or all the layers of open porous metal 100 contact bone B, thereby providing initial fixation of orthopaedic implant 600' within void V.

As with orthopaedic implant 600 (FIG. 7), orthopaedic implant 600' may be combined with one or more bone growth factors (either within the layers of open porous metal component 100 or within resorbable bone growth promoting component 200). Also, one or more layers of resorbable bone growth promoting component 200 of orthopaedic implant 600' may comprise a soft mass composition as opposed to the solid mass (compressed powder) depicted in FIG. 8. Further, as with other embodiments of the orthopaedic implants described herein, during implantation, orthopaedic implant 600' may be shaped and sized according to a particular need.

Referring to FIG. 9a, yet another configuration of orthopaedic implant 600" is depicted. Orthopaedic implant 600" comprises three layers of open porous metal component 100 and two layers of resorbable bone growth promoting component 200, arranged in multiple, alternating layers. Unlike the configurations of orthopaedic implant 600, 600', shown in FIGS. 7 and 8, FIG. 9a illustrates an exemplary embodiment of orthopaedic implant 600" comprising a manufacturer-constructed configuration, which may be used in conjunction with commercially available prostheses, such as femoral stem 650 and distal femoral articulating component 660, shown in FIG. 9a.

As illustrated in FIG. 9a, orthopaedic implant 600" is configured to secure femoral stem 650 which, in use, is implanted within the distal femoral canal C of femur F, to distal femoral articulating component 660. According to the configuration of orthopaedic implant 600" shown in FIG. 9a, distal segment 652 of femoral stem 650 fits within stem receiving area 610 defined by orthopaedic implant 600". Distal segment 652 may be secured within stem receiving area 610 by compression fit, an adhesive, or a screw or the like. Further, in some configurations, femoral stem 650 may be comprised of open porous metal component 100, thereby allowing for femoral stem 650 and orthopaedic implant 600" to become rigidly affixed by way of bone ingrowth.

Distal region 620 of orthopaedic implant 600" is shaped and sized to securely attach to augment receiving section 662 of distal femoral articulating component 660. For example, distal region 620 of orthopaedic implant 600" may fit, and be secured within, augment receiving section 662 by way of compression fit, a screw, or an adhesive. Further, although distal region 620 of orthopaedic implant 600" is shown as comprising open porous metal component 100, in some configurations only certain portions of distal region 620 (such as tissue contacting areas) will comprise open porous metal component 100. In such configurations, the non-open porous metal portions of distal region 620 may comprise materials typically used in orthopaedic implants such as ceramics, titanium, and plastic alloys. Even further, some configurations of orthopaedic implant 600" may include distal region 620 being comprised completely of one or more materials typically used in orthopaedic implants.

Additionally, as with other configurations of the orthopaedic implants disclosed herein, orthopaedic implant 600" may be combined with one or more growth factors. Further, while orthopaedic implant 600" is described and depicted as a being preshaped and sized (for example by a manufacturer), in some configurations orthopaedic implant 600" may still be modified by a surgeon during surgery. For example, a surgeon may be able to custom trim portions of orthopaedic implant 600" during surgery to provide a desired fit and shape for a specific patient need.

Referring again to FIGS. 7, 8, and 9a, when implanted, the illustrative configurations of orthopaedic implant 600, 600', 600" promote new bone regeneration through orthopaedic implant 600, 600', 600" and provide initial structural support and fixation for prosthesis. As detailed above, the layers of resorbable bone growth promoting component 200 (of orthopaedic implant 600, 600', 600") provide a temporary matrix for cell proliferation and extracellular matrix deposition, which also promotes vascularization for supporting continued bone regeneration and maintenance. As new bone is regenerated, resorbable bone growth promoting component 200 is resorbed into the new bone.

As detailed above, open porous metal component 100 aides in initial fixation of orthopaedic implant 600, 600', 600" with prosthesis P and bone B, and provides structural support for prosthesis P. Open porous metal component 100 also provides a matrix which supports bone ingrowth and mineralization therein which, upon bone ingrowth therein, forms a rigid and secure secondary fixation of orthopaedic implant 600, 600', 600" to bone B and prosthesis P.

Further, as described herein, orthopaedic implant 600, 600', 600" maybe combined with one or more bone growth factors or agents. For example, the osteoconductive carrier comprising resorbable bone growth promoting component 200, and/or open porous metal 100, may be combined with one or more bone growth factors or agents. Such configurations, upon implantation, promote the initiation of osteogensis, thereby further aiding in the regeneration of bone and the fixation of natural bone throughout orthopaedic implant 600, 600', 600".

Figure 9B:
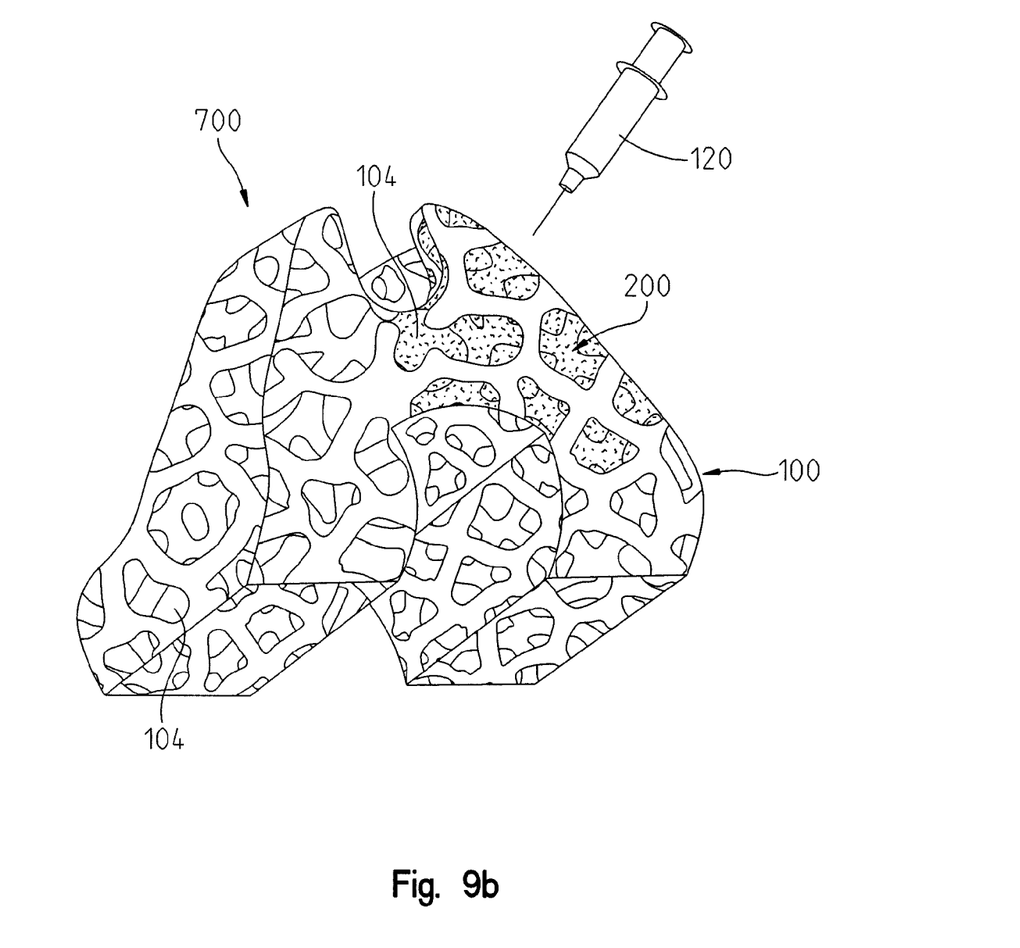

Referring to FIG. 9b, an illustrative embodiment of orthopaedic implant 700 is presented. As with orthopaedic implant 600" depicted in FIG. 9a, orthopaedic implant 700 comprises a manufacturer-constructed configuration, which may be used in conjunction with commercially available prostheses, such as femoral stem S and distal femoral abutment A shown in FIG. 9a. However, unlike orthopaedic implant 600" presented in FIG. 9a, orthopaedic implant 700 is entirely comprised of open porous metal component 100 with resorbable bone growth promoting component 200 (comprising a soft mass) being disposed within channels 104. Advantageously, orthopaedic implant 700 provides greater initial support for prosthesis P than provided by the configuration of orthopaedic implant 600" shown in FIG. 9a.

In some configurations, resorbable bone growth promoting component 200 may be inserted into channels 104 of orthopaedic implant 700 by a surgeon prior to, or during surgery. Such configurations advantageously permit a surgeon to prepare resorbable bone growth promoting component 200 to desired composition and concentration. In other configurations of orthopaedic implant 700, resorbable bone growth promoting component 200 may constitute a powder, or putty-like composition, which is inserted into channels 104 during manufacture. Such configurations may then be combined with a desired liquid, such as bone marrow aspirate, blood plasma, or other mixtures as disclosed herein. Further, while shown in FIG. 9b as being disposed within only a portion of channels 104 of orthopaedic implant 700, resorbable bone growth promoting component 200 may be disposed throughout all, or substantially all, channels 104 of orthopaedic implant 700.

Additionally, as described herein, orthopaedic implant 700 may be combined with one or more growth factors or agents. For example, as described herein, resorbable bone growth promoting component 200 (disposed within channels 104 of open porous metal component 100) may have one or more growth factors embedded therein. Such configurations, upon implantation, promote the initiation of osteogensis throughout open porous metal component 100 comprising orthopaedic implant 700.

When implanted, orthopaedic implant 700 promotes new bone regeneration throughout channels 104 and provides structural support and fixation for the bone, joint or other prosthesis components. As detailed above, resorbable bone growth promoting component 200 (disposed throughout channels 104 of open porous metal component 100 comprising orthopaedic implant 700) provides a temporary matrix for cell proliferation and extracellular matrix deposition. Further, resorbable bone growth promoting component 200 promotes vascularization (throughout orthopaedic implant 700) for supporting continued bone regeneration and maintenance. As new bone is regenerated, resorbable bone growth promoting component 200 is resorbed into the new bone, which is ingrown within channels 104 of orthopaedic implant 700, thereby creating a rigid, solid affixation of the surrounding bone to orthopaedic implant 700.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. An orthopedic implant, comprising:
    a three-dimensional augment body including a plurality of stacked layers, said plurality of stacked layers comprising a first porous metal layer and a second porous metal layer, wherein said first porous metal layer and said second porous metal layer are separately formed layers, and wherein said three-dimensional augment body incorporates a resorbable bone growth-promoting component;
    an implantable prosthesis for implantation adjacent said three-dimensional augment body; and
    a bone cement layer attaching said implantable prosthesis to said three-dimensional augment body.

2. The orthopedic implant of claim 1, wherein said first porous metal layer and said second porous metal layer each have a porosity between 55% and 90%.

3. The orthopedic implant of claim 1, wherein said first porous metal layer and said second porous metal layer are malleable.

4. The orthopedic implant of claim 1, wherein said resorbable bone growth-promoting component comprises a growth factor.

5. The orthopedic implant of claim 1, wherein said first porous metal layer and said second porous metal layer are spaced from one another in said three-dimensional augment body.

6. The orthopedic implant of claim 1, wherein said resorbable bone growth-promoting component includes a resorbable bone growth-promoting layer forming part of said plurality of stacked layers.

7. The orthopedic implant of claim 6, wherein said resorbable bone growth-promoting layer is situated between said first porous metal layer and said second porous metal layer.

8. The orthopedic implant of claim 7, wherein said resorbable bone growth-promoting layer separates said first porous metal layer from said second porous metal layer.

9. The orthopedic implant of claim 8, wherein said first porous metal layer and said second porous metal layer each comprise a coefficient of friction that is greater than said resorbable bone growth-promoting layer and mammalian bone tissue.

10. The orthopedic implant of claim 1, wherein said resorbable bone growth-promoting component includes a bone growth agent embedded in at least one of said first porous metal layer and said second porous metal layer.

11. The orthopedic implant of claim 1, wherein said implantable prosthesis is a knee, hip or shoulder prosthesis.

12. The orthopedic implant of claim 1, wherein said implantable prosthesis includes an elongate stem component, and wherein said three-dimensional augment body provides an elongate passage into which said elongate stem component can be received.

13. An orthopedic implant, comprising:
    a three-dimensional augment body including a first porous metal layer stacked with a second porous metal layer with a resorbable bone growth-promoting layer situated between said first porous metal layer and said second porous metal layer, wherein said first porous metal layer and said second porous metal layer are separately formed layers;
    an implantable prosthesis for implantation adjacent said three-dimensional augment body; and
    a bone cement layer attaching said implantable prosthesis to said three-dimensional augment body.

14. The orthopedic implant of claim 13, wherein said first porous metal layer and said second porous metal layer each have a porosity between 55% and 90%.

15. The orthopedic implant of claim 13, wherein said resorbable bone growth-promoting layer separates said first porous metal layer from said second porous metal layer.

16. The orthopedic implant of claim 13, wherein said first porous metal layer and said second porous metal layer each comprise a coefficient of friction that is greater than said resorbable bone growth-promoting layer and mammalian bone tissue.

17. The orthopedic implant of claim 13, wherein said resorbable bone growth-promoting layer extends into at least one of said first porous metal layer from said second porous metal layer.

18. The orthopedic implant of claim 13, wherein the implantable prosthesis comprises a knee, hip or shoulder prosthesis with an elongate stem component, wherein said three-dimensional augment body provides a passage into which said elongate stem component can be received.

19. The orthopedic implant of claim 13, wherein said resorbable bone growth-promoting layer includes a first bone growth agent, and wherein said three-dimensional augment body includes a second bone growth agent embedded in at least one of said first porous metal layer and said second porous metal layer.

* * * * *